(12) United States Patent
Srivathsa et al.

(10) Patent No.: US 11,482,323 B2
(45) Date of Patent: Oct. 25, 2022

(54) ENHANCING PATIENT CARE VIA A STRUCTURED METHODOLOGY FOR WORKFLOW STRATIFICATION

(71) Applicant: Rauland-Borg Corporation, Mount Prospect, IL (US)

(72) Inventors: Karthik Srivathsa, Palatine, IL (US); Timothy Keller, Bristol, IL (US)

(73) Assignee: Rauland-Borg Corporation, Mount Prospect, IL (US)

( * ) Notice: Subject to any disclaimer, the term of this patent is extended or adjusted under 35 U.S.C. 154(b) by 377 days.

(21) Appl. No.: 16/590,005

(22) Filed: Oct. 1, 2019

(65) Prior Publication Data

US 2021/0098116 A1     Apr. 1, 2021

(51) Int. Cl.
| | |
|---|---|
| *H04L 29/08* | (2006.01) |
| *G06Q 50/22* | (2018.01) |
| *G16H 40/20* | (2018.01) |
| *G16H 10/60* | (2018.01) |
| *G06N 20/00* | (2019.01) |
| *H04W 4/021* | (2018.01) |
| *H04W 4/12* | (2009.01) |
| *H04W 88/02* | (2009.01) |

(52) U.S. Cl.
CPC ............ *G16H 40/20* (2018.01); *G06N 20/00* (2019.01); *G16H 10/60* (2018.01); *H04W 4/021* (2013.01); *H04W 4/12* (2013.01); *H04W 88/02* (2013.01)

(58) Field of Classification Search
CPC ........ G16H 40/20; G16H 10/60; G16H 50/70; G06N 20/00; G06N 5/025; H04W 4/021; H04W 4/12; H04W 88/02; G06Q 10/0631; G06Q 10/063114; G06Q 10/063116; G06Q 10/0633
See application file for complete search history.

(56) References Cited

U.S. PATENT DOCUMENTS

| | | |
|---|---|---|
| 5,838,223 A | 11/1998 | Gallant et al. |
| 6,097,288 A | 8/2000 | Koeppe, Jr. |
| D527,011 S | 8/2006 | Bixler |
| (Continued) | | |

FOREIGN PATENT DOCUMENTS

WO    WO 2019/142370 A1    7/2019

OTHER PUBLICATIONS

Guo et al. "A ZigBee Network Application in Emergency Exit Guiding," 2010 International Computer Symposium (ICS2010), 91-94 (2010).

(Continued)

*Primary Examiner* — Maroun P Kanaan
(74) *Attorney, Agent, or Firm* — Leydig, Voit & Mayer, Ltd.

(57) ABSTRACT

A system, device and method are provided for modifying workflows in a hospital environment. The system includes a workflow stratification server configured to receive and analyze event messages from a nurse call system and interface devices. The workflow stratification server determines a current state of the hospital environment and relevant applicable conditions for each event message identified as a trigger event. That way, the workflow stratification server prioritizes the trigger events and provides responses to the trigger events in a manner that takes into account resources in the hospital environment.

20 Claims, 6 Drawing Sheets

(56) References Cited

U.S. PATENT DOCUMENTS

| | | |
|---|---|---|
| 7,292,135 B2 | 11/2007 | Bixler et al. |
| 7,333,002 B2 | 2/2008 | Bixler et al. |
| 7,526,529 B2 | 4/2009 | Unluturk et al. |
| 8,032,403 B2 | 10/2011 | Gremont et al. |
| 8,806,473 B2 | 8/2014 | Birtwhistle et al. |
| 9,299,238 B1 | 3/2016 | Ahmad et al. |
| 2002/0138328 A1 | 9/2002 | Arning et al. |
| 2003/0074222 A1 | 4/2003 | Rosow et al. |
| 2004/0145481 A1 | 7/2004 | Dilbeck et al. |
| 2005/0075902 A1 | 4/2005 | Wager et al. |
| 2006/0049936 A1 | 3/2006 | Collins et al. |
| 2006/0111939 A1 | 5/2006 | Bixler et al. |
| 2006/0112187 A1 | 5/2006 | Unluturk et al. |
| 2006/0267740 A1 | 11/2006 | Bixler et al. |
| 2007/0192174 A1 | 8/2007 | Bischoff |
| 2007/0210910 A1 | 9/2007 | Norstrom et al. |
| 2007/0288285 A1 | 12/2007 | Nilsson |
| 2009/0212925 A1 | 8/2009 | Schuman, Sr. et al. |
| 2009/0313659 A1 | 12/2009 | Samuels |
| 2010/0169150 A1 | 7/2010 | Gremont et al. |
| 2010/0191543 A1 | 7/2010 | Schuman |
| 2010/0217618 A1 | 8/2010 | Piccirillo et al. |
| 2010/0305973 A1 | 12/2010 | McLaren et al. |
| 2011/0007883 A1 | 1/2011 | Bingham et al. |
| 2011/0112877 A1 | 5/2011 | Govind et al. |
| 2011/0208541 A1 | 8/2011 | Wilson et al. |
| 2011/0246220 A1 | 10/2011 | Albert |
| 2012/0028589 A1 | 2/2012 | Fan et al. |
| 2012/0329420 A1 | 12/2012 | Zotti et al. |
| 2013/0264074 A1 | 10/2013 | Lewis et al. |
| 2013/0323699 A1 | 12/2013 | Edwards et al. |
| 2014/0024333 A1 | 1/2014 | Stadtlander |
| 2014/0132393 A1 | 5/2014 | Evans |
| 2014/0244819 A1 | 8/2014 | Patrick et al. |
| 2014/0327519 A1 | 11/2014 | Carroll et al. |
| 2014/0379357 A1 | 12/2014 | Srivathsa et al. |
| 2015/0109442 A1 | 4/2015 | Derenne et al. |
| 2015/0339407 A1 | 11/2015 | Gallo et al. |
| 2016/0165369 A1 | 6/2016 | Perkins et al. |
| 2017/0039823 A1 | 2/2017 | Srivathsa et al. |
| 2017/0257400 A1 | 9/2017 | Peters et al. |
| 2018/0082573 A1* | 3/2018 | Zuckerman ............ A61B 5/747 |
| 2018/0137943 A1* | 5/2018 | Webb, III ............ G06F 16/252 |
| 2018/0162413 A1 | 6/2018 | Theodosiou |
| 2018/0330813 A1 | 11/2018 | Garber et al. |
| 2019/0088097 A1 | 3/2019 | Jacobs |
| 2019/0295207 A1 | 9/2019 | Day et al. |

OTHER PUBLICATIONS

European Patent Office, International Search Report and the Written Opinion in International Application No. PCT/US2020/053706 (dated Jan. 18, 2021).

European Patent Office, International Preliminary Report on Patentability in International Application No. PCT/US2020/053706 (dated Apr. 4, 2022).

* cited by examiner

ENHANCING PATIENT CARE VIA A STRUCTURED METHODOLOGY FOR WORKFLOW STRATIFICATION

BACKGROUND

A typical hospital includes many care units, such as an Intensive Care Unit (ICU), a Cardiology Unit, an Emergency Care Unit, a General Surgery Unit, an Oncology Unit, a Pediatrics Unit, and a Pharmacy Unit, among others. Further, each of these units requires associated staff members and equipment to provide care for patients of the hospital.

Hospitals generally use a nurse call system to alert staff of varying needs of support in the hospital. Typically, a nurse call system is implemented over a hospital's internal network and utilized to update staff as to needed support within the care units of the hospital. The needed support is generally handled by a staff member assigned to a specific location and level of support within a hospital/hospital care unit.

In addition to the nurse call system, hospitals include a variety of medical devices. Over time, the medical devices have developed such that they generate various types of data that can be communicated to a nurse call system over the hospital's internal network. However, there may not be an overall high-level view of all generated data from all the variety of medical devices. Thus, event messages that may influence one another or that may be related to one another may not be efficiently linked together to adjust workflows in the hospital.

In addition to the variety of medical devices, a hospital may also include an Admit Discharge Transfer (ADT) system and Real Time Location Service (RTLS) system that also provide event messages to the hospital's internal network, and also may communicate those event messages separate from the hospital's a nurse call system. Therefore, event messages from the ADT system and the RTLS system may not be considered or readily available to the nurse call system when undergoing a workflow.

In view of the above, there is a need for a system that will monitor event messages from hospital medical devices, ADT systems, RTLS systems, nurse call systems, and other various network enabled hospital devices in order to determine appropriate workflows or to dynamically adjust workflows for responding to generated events.

SUMMARY

In a particular embodiment, a workflow stratification system for adjusting workflows within a hospital environment is provided. The workflow stratification system includes: a plurality of interface devices associated with the hospital environment; a communication network coupled to each of the plurality of interface devices; a plurality of nurse call devices comprised in a nurse call system of the hospital environment; a nurse call server coupled to the communication network, wherein the nurse call server is configured to communicate with each of the plurality of nurse call devices, and wherein the nurse call server is comprised in the nurse call system; and a workflow stratification server communicatively coupled to the nurse call server and the plurality of interface devices. The workflow stratification server is configured to: receive event messages from the plurality of interface devices and from the plurality of nurse call devices; evaluate a current state in context of the event messages, the current state being a cluster of event messages; determine relevant applicable conditions for trigger events, trigger events being a subset of the event messages, wherein each relevant application condition is a subset of the cluster of event messages; analyze the trigger events to determine a priority for responding to the trigger events; and remove one or more of the trigger events based on receiving termination conditions.

In another embodiment, a method for adjusting workflows within a hospital environment is provided. The hospital environment including a plurality of interface devices, a communication network coupled to each of the plurality of interface devices, a nurse call server, a plurality of nurse call devices communicatively coupled to the nurse call sever, and a workflow stratification server communicatively coupled to the nurse call server and the plurality of interface devices. The method includes: receiving event messages from the plurality of interface devices and from the plurality of nurse call devices; evaluating a current state in context of the event messages, the current state being a cluster of event messages; determining relevant applicable conditions for trigger events, trigger events being a subset of the event messages, wherein each relevant application condition is a subset of the cluster of event messages; analyzing the trigger events to determine a priority for responding to the trigger events; and removing one or more of the trigger events based on receiving termination conditions.

In yet another embodiment, a workflow stratification server for adjusting workflows within a hospital environment is provided. The hospital environment including a plurality of interface devices, a communication network coupled to each of the plurality of interface devices, a nurse call server, and a plurality of nurse call devices communicatively coupled to the nurse call sever. The nurse call server is communicatively coupled to the workflow stratification sever and the plurality of interface devices. The workflow stratification server includes: a processor; and a memory storing instructions that when executed by the processor configure the workflow stratification server to perform steps including: receiving event messages from the plurality of interface devices and from the plurality of nurse call devices; evaluating a current state in context of the event messages, the current state being a cluster of event messages; determining relevant applicable conditions for trigger events, trigger events being a subset of the event messages, wherein each relevant application condition is a subset of the cluster of event messages; analyzing the trigger events to determine a priority for responding to the trigger events; and removing one or more of the trigger events based on receiving termination conditions.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
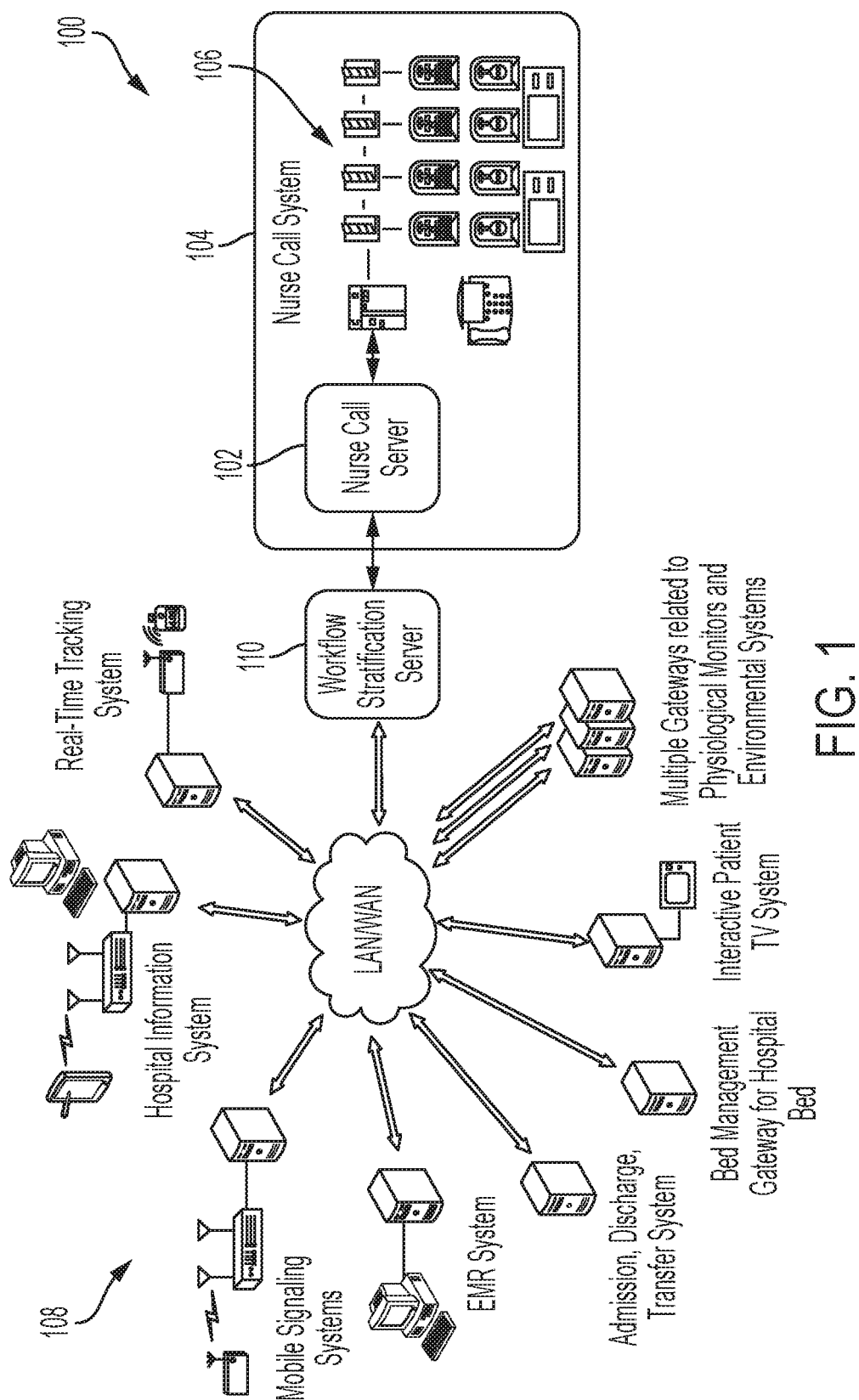
FIG. 1 is a block diagram illustrating a system for event messages in a hospital, according to an example embodiment.

Hospitals generally use a nurse call system to alert staff of varying needs of support in the hospital. A nurse call system is usually implemented over a hospital's internal network and utilized to update staff as to needed support patients. Due to the hospital being divided into different care units, needed support is generally handled by a staff member assigned to a specific location or level of support within the hospital/hospital care unit. This balkanization of staff members to specific areas or to specific patients can underutilize some staff members while over-utilizing others.

In addition to the nurse call system, hospitals include a variety of patient medical devices. Over time, the patient medical devices have developed such that they generate various types of data that can be communicated to a nurse call system over the hospital's internal network. In addition to the variety of medical devices, a hospital may also include an ADT system and RTLS system that also provide event messages to the hospital's internal network. A hospital can integrate these systems in a manner such that event messages are provided to a workflow stratification server. That way, the workflow stratification server receives event messages from integrated systems in the hospital, including the nurse call system, in order to suggest new workflows or pre-programmed workflows to caregivers in the hospital.

A workflow is generally a series of actions taken within the hospital environment resulting from a particular event within the hospital, such as when a button is pressed, time trigger is activated, staff initiates via a trigger on a system user interface, a rule based trigger occurs or even absence of action in certain conditions. Static workflows exist in hospitals, and they determine what staff members do once the button on the nurse call system is pressed or once an outstanding call is present in the nurse call system queue. Static workflows are not equipped to handle difficulty associated with a hospital environment which is constantly changing. Scheduled personnel may not always be available, or a patient may be a fall risk and is not supposed to get out of the bed. In these situations, the hospital needs to be able to work with available personnel and needs to be able to respond quickly when a fall risk patient gets out of bed.

Conditions in a hospital are dynamic but workflows are not. Embodiments of the disclosure provide a system and methodology for evaluating a set of conditions and executing one of many preprogrammed or learned process workflows. The system provides advantages in a hospital environment which include provision of faster call response, correct caregiver response, reduction of alarm fatigue, and assured patient safety.

Care needs for patients are dynamic, therefore, workflows for taking care of patients cannot be static. Given that patient safety is at risk, embodiments of the disclosure advocate a pre-programmed (yet flexible) workflow. That is, the workflow can be refined based on user feedback and machine learning algorithms. Components of such a workflow include a path for normal flow, i.e., a typical workflow, and definitions for variations to the normal flow, i.e., alternate workflows including exception workflows.

In an embodiment, configuration of workflows accommodates who executes the workflow, the type of workflow (e.g., clinical or non-clinical), a current state of the user and patient (if the user is a staff member), a ranking of the current workflow relative to other workflows, and so on. Each workflow can be defined as sequence of instructions along with associated triggers (or timeout), conditional logic with branching and looping constructs and notification targets where applicable. Workflows have a defined start state and a defined end state. In an embodiment, workflows explicitly define rollback/cleanup rules should one or more steps encounter exceptions that force an abnormal termination.

In an embodiment, a normal workflow is triggered by a person or role of the user. In case of a pillow speaker button, the typical user is a patient. Should the patient push a pillow speaker button, the system may execute the normal workflow. Alternate workflows, on the other hand, are executed by a caregiver (staff of the care provider by type of skill) or a family member. The alternate workflows can potentially notify a care team (as opposed to a caregiver) and execute at a higher relative priority to the normal workflow, since a staff member is seeking assistance in that situation.

In an embodiment, a normal workflow is automatically triggered when specific conditions exist. For example, should a patient get up from her bed, the bed can detect the movement and signal a workflow stratification server to execute a workflow. The workflow stratification server in cooperation with the hospital's nurse call system can execute the normal workflow if the patient is not flagged as a "fall risk." However, the workflow stratification server can trigger one or more workflows should the patient be flagged as a "fall risk." In an embodiment, the "fall risk" flag can be further categorized into a high, medium, or low "fall risk," and the workflow stratification server can work with the nurse call system to determine an appropriate workflow based on the "fall risk" category. Embodiments of the disclosure provide algorithms or structured methodologies for identifying which workflows to execute when a call is placed from a patient room.

Embodiments of the disclosure provide a workflow stratification system that determines which workflows to execute based on various conditions. These conditions include available staff in a hospital patient's room, staff assigned to the patient, role of individual initiating the workflow, clinical or non-clinical application, interdepartmental, ancillary, and so on. Advantages of adopting the workflow stratification system include increased safety, increased productivity, increased patient satisfaction, minimization of financial risk (liability), and increased revenue.

Embodiments of the disclosure are described in greater detail based on the figures. All features described and/or illustrated herein can be used alone or combined in different combinations in embodiments of the invention. FIG. 1 illustrates a block diagram of a hospital's internal network 100. The network 100 includes a nurse call server 102 that communicates with a nurse call system 104 that includes nurse call devices 106. The nurse call devices 106 are generally devices such as corridor lights, bedside stations, bath stations, emergency call stations, a Session Initiation Protocol (SIP) interface, a personal computer (PC) console communicatively coupled to the hospital's internal network 100, a TAP interface, a patient station, and a staff terminal.

The nurse call server 102 connects to a workflow stratification server 110. The workflow stratification server 110 interfaces the hospital medical devices and other systems, such as the ADT system and the RTLS system, to the nurse call server 102. For convenience, the hospital medical devices and other systems will collectively be referred to as a plurality of interface devices 108. These interface devices 108 are distributed throughout a hospital's various individual care units and communicate with the workflow stratification server 110 through communication network 111. FIG. 1 contains a non-exhaustive listing of possible interface devices 108, such as a hospital information system (HIS), a RTLS system, an interactive patient television system, an Electronic Medical Record (EMR) system, an ADT system, a bed management gateway, a physiological monitor gateway, and a mobile signaling application gateway.

In certain embodiments, the nurse call server 102 may be formed from a plurality of interconnected servers or a plurality of services running on an individual server. Further, in certain embodiments, the workflow stratification server 110 may be formed from a plurality of interconnected servers or a plurality of services running on an individual server. While in other embodiments, the nurse call server 102 and the workflow stratification server 110 may be integrated into a single server cluster device. Additionally, in other embodiments, the nurse call server 102 and the workflow stratification server 110 may be implemented as cloud servers.

Regardless of the structural server implementation, the workflow stratification server 110 receives triggers, events, and status from the interface devices 108 and the nurse call server 102 and thereby the nurse call system 104. The workflow stratification server 110 communicates and cooperates with the nurse call system 104 to execute and manage workflows in the hospital's internal network 100. In an embodiment, the communication is facilitated over an extensible markup language (XML) interface hosted by the workflow stratification server 110 that translates event messages received from both the interface devices 108 and the nurse call devices 106, determines workflows and responses for the event messages, and activates appropriate nurse call devices 106 or interface devices 108 based on a chosen workflow or workflows.

Figure 2:
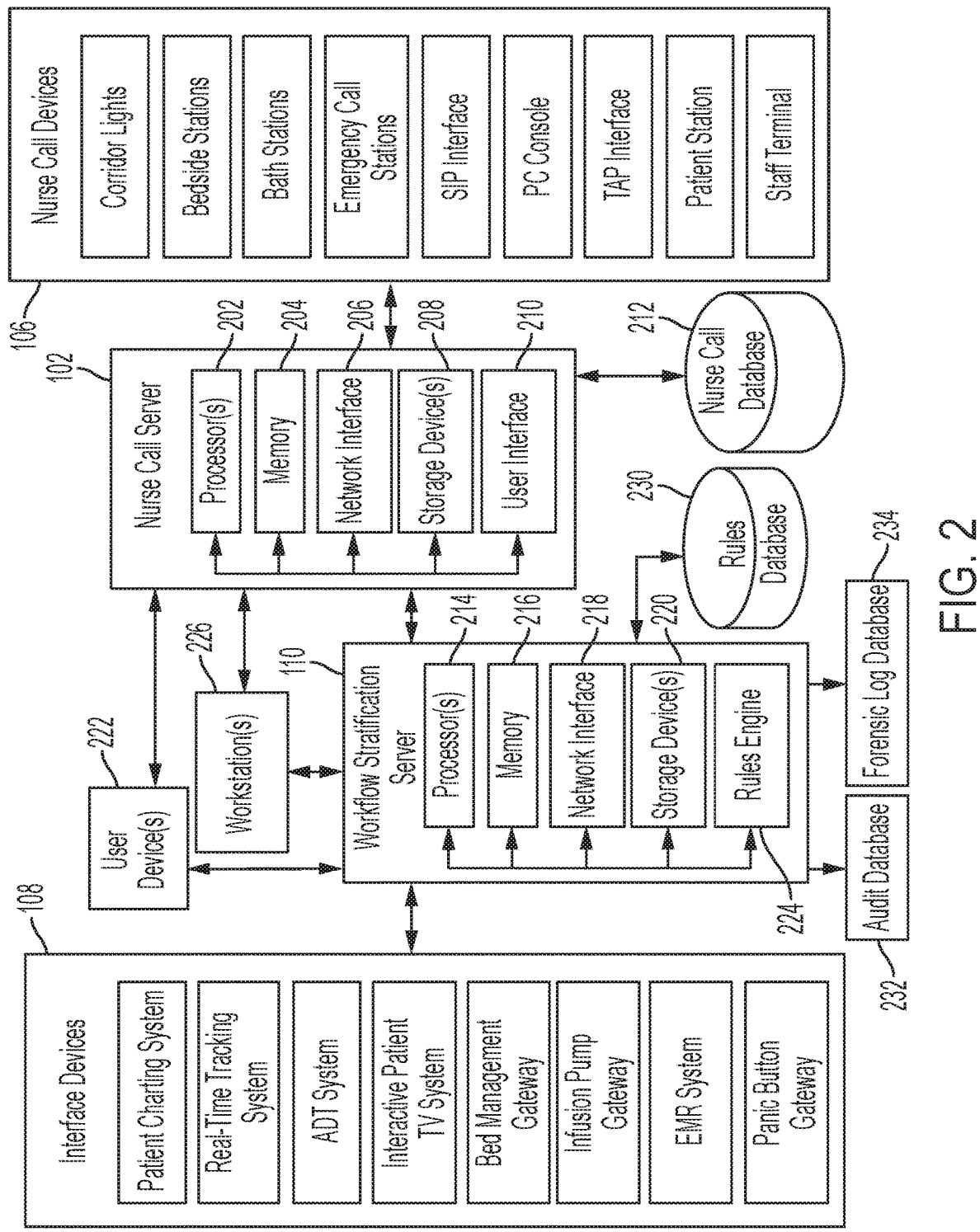
FIG. 2 is a block diagram illustrating components of a workflow stratification server and nurse call server of FIG. 1, according to an example embodiment.

FIG. 2 provides a block diagram of the nurse call server 102 and the workflow stratification server 110 from FIG. 1, according to one embodiment of the disclosure. The nurse call server 102 includes one or more processors 202, memory 204, a network interface 206, one or more storage devices 208, and a user interface (UI) 210. In some embodiments, each of the components including the processor(s) 202, the memory 204, the network interface 206, the storage device(s) 208 and the UI 210 are interconnected physically, communicatively, and/or operatively for inter-component communications.

As illustrated, processor(s) 202 are configured to implement functionality and/or process instructions for execution within server 102. For example, processors 202 execute instructions stored in memory 204 or instructions stored on storage devices 208. Memory 204, which may be a non-transient, computer-readable storage medium, is configured to store information within server 102 during operation. In some embodiments, memory 204 includes a temporary memory, i.e. an area for information not to be maintained when the server 102 is turned off. Examples of such temporary memory include volatile memories such as random access memories (RAM), dynamic random access memories (DRAM), and static random access memories (SRAM). Memory 204 also maintains program instructions for execution by the processors 202.

Storage devices 208 also include one or more non-transient computer-readable storage media. Storage devices 208 are generally configured to store larger amounts of information than memory 204. Storage devices 208 may further be configured for long-term storage of information. In some examples, storage devices 208 include non-volatile storage elements. Non-limiting examples of non-volatile storage elements include magnetic hard discs, optical discs, floppy discs, flash memories, or forms of electrically programmable memories (EPROM) or electrically erasable and programmable (EEPROM) memories.

The nurse call server 102 uses network interface 206 to communicate with external devices via one or more networks, such as the network 111 of FIG. 1. Such networks may include one or more wireless networks, wired networks, fiber optics networks, and other types of networks through which communication between the nurse call server 102 and an external device may be established. Network interface 206 may be a network interface card, such as an Ethernet card, an optical transceiver, a radio frequency transceiver, or any other type of device that can send and receive information.

UI 210 is a network application hosted on the nurse call server 102 and provided over the network 111. In this regard, UI 210 acts to provide a user access to the nurse call server 102. This allows a user to change settings within the nurse call server 102 to customize nurse call functionality provided by the nurse call system 104 (see FIG. 1). In an embodiment, the user may use user devices 222 or workstations 226 to change settings within the nurse call server 102 over the network 111.

In certain embodiments, the nurse call server 102 accesses a nurse call database 212. The nurse call database 212 stores locations within the hospital environment and hospital staff and nurse call devices 106 located within the various locations. In this manner, the nurse call system 104 (see FIG. 1) can route data to the appropriate hospital staff member via the appropriate nurse call device 106, such as a staff terminal.

FIG. 2 further illustrates the workflow stratification server 110 coupled to the nurse call server 102. The workflow stratification server 110 includes one or more processors 214, memory 216, a network interface 218, one or more storage devices 220, and a rules engine 224. In some embodiments, each of the components including the processor(s) 214, the memory 216, the network interface 218, the storage device(s) 220, and the rules engine 224 are interconnected physically, communicatively, and/or operatively for inter-component communications.

As illustrated, processor(s) 214 are configured to implement functionality and/or process instructions for execution within the workflow stratification server 110. For example, processors 214 execute instructions stored in memory 216 or instructions stored on storage devices 218. Memory 216, which may be a non-transient, computer-readable storage medium, is configured to store information within workflow stratification server 110 during operation. In some embodiments, memory 216 includes a temporary memory, i.e. an area for information not to be maintained when the workflow stratification server 110 is turned off. Examples of such temporary memory include volatile memories like RAM, DRAM, and SRAM. Memory 216 also maintains program instructions for execution by the processors 214.

Storage devices 220 also include one or more non-transient computer-readable storage media. Storage devices 220 are generally configured to store larger amounts of information than memory 216. Storage devices 220 may further be configured for long-term storage of information. In some examples, storage devices 220 include non-volatile storage elements. Non-limiting examples of non-volatile storage elements include magnetic hard discs, optical discs, floppy discs, flash memories, or EPROM or EEPROM.

The workflow stratification server 110 uses network interface 218 to communicate with external devices, such as the interface devices 108 via the communication network 111 (see FIG. 1). This communication may occur over one or more wireless networks, wired networks, fiber optics networks, and other types of networks through which communication between the workflow stratification server 110 and the interface devices 108 may be established. Network interface 218 may be a network interface card, such as an Ethernet card, an optical transceiver, a radio frequency transceiver, or any other type of device that can send and receive information.

Rules engine 224 is an application hosted on the workflow stratification server 110. The rules engine 224 enables the workflow stratification server 110 to accommodate to environmental changes in the hospital. For example, the rules engine 224 makes rules to assist the workflow stratification server 110 to change workflows based on event messages received from interface devices 108 and nurse call devices 106 via the nurse call server 102. The rules engine 224 can develop algorithmic rules, e.g., alerting a closest staff member to check on a patient when specific situations arise based on event messages received. The rules engine 224 can incorporate machine learning, allowing the workflow stratification server 110 to learn rules based on observed behavior, thus constructing a rule for execution. The rules engine 224 can take historical data into account, storing the data in a rules database 230. The rules engine 224 can further apply big data tools to develop rules for altering workflows in the hospital. The workflow stratification server 110 can take advantage of the rules database 230 to support big data tools. The rules database 230 can organize rules in an efficient manner and the workload stratification server 110 can use extract, transform, and load (ETL) general procedures to access information stored in the rules database 230.

The rules engine 224 of the workflow stratification server 110 further utilizes an audit database 232 and a forensic log database 234. After rules engine 224 creates a rule based on various events and triggers within the hospital's internal network 100 (see FIG. 1), that rule and its associated events and triggers are stored within both the audit database 232 and the forensic log database 234. The audit database 232 functions as long term storage of rules and associated events and triggers, and the forensic log database 234 functions as a short term storage for the rules and their associated events and triggers. The data stored in the audit database 232 allows for subsequent review of events and responses/rules created by the workflow stratification server 110 by hospital personnel. The data stored in the forensic log database 234 allows for technical troubleshooting of the system in case of a failure of a component or the entire system.

As an aside, in certain embodiments, the rules engine 224 may be implemented on dedicated processor and memory devices of the workflow stratification server 110. Alternatively, in other embodiments, the rules engine 224 may represent various states of the processor 214, and are defined by program instructions and/or data stored on the memory 216 or the storage device 220.

Using the above described system components of the hospital's internal network 100 (see FIG. 1), the following exemplary descriptions of system use cases will be described. The exemplary system operation descriptions are related to (1) managing care for a fall risk patient, (2) managing staffing levels, (3) managing automated systems within a patient's room, and (4) managing a cleaning schedule for the patient's room.

In a first exemplary system operation, care for a fall risk patient can be enhanced by the workflow stratification server 110. Conventionally, in a hospital, after a patient falls, the patient pushes a button to alert a caregiver that he needs help getting up. Embodiments of the disclosure improve upon the conventional setting in that the workflow stratification server 110 can receive event messages or triggers from sensors on the patient's hospital bed. For example, the workflow stratification server 110 can receive triggers from the nurse call server 102 when a side rail of the patient's bed is being lowered. The workflow stratification server 110 can receive from the patient's chart or medical record that the patient is a fall risk. By the time the patient pushes the button to alert a caregiver, the workflow stratification server 110 combined the fall risk along with the side rail of the patient's bed being lowered to make a decision to escalate the call that the patient places.

For the fall risk, the workflow stratification server 110 can route important calls to the closest caregiver able to provide assistance. For patients who are not a fall risk, the side rail of the patient's bed being lowered is not considered and will not escalate the call that the patient places or will not automatically place a call. This can reduce multiple notifications about a patient getting out of a bed and will help reduce or eliminate alarm fatigue experienced by caregivers in the hospital. As such, the workflow stratification server 110 helps the caregiver prioritize handling more important calls for patients that should not get up from bed without assistance. As indicated in this example, a standard workflow is adjusted based on receiving additional information about the patient, i.e., the patient being a fall risk. The additional information allows for events to be scrutinized differently; e.g., the side rail of the patient's bed being lowered is treated differently. The workflow stratification server 110, being able to receive event messages from interface devices 108 and nurse call devices 106 can help efficiently manage patient care.

In a second exemplary system operation, the workflow stratification server 110 can assist in effectively deploying staff for patient care when an assigned caregiver is unavailable to help. For example, the assigned caregiver gave a late notice that she would not be in at work that day, or she is stuck in traffic and is unable to get to work at the beginning of her shift. The workflow stratification server 110 can receive staffing information from check-in systems or from real-time tracking systems. By receiving an event message indicating that certain patients may exhibit higher wait times due to their assigned caregiver not being present, the workflow stratification server 110 can temporarily reallocate or reassign caregivers currently on-site to take care of patients they are not usually assigned to. This could be used to help alleviate wait times for helping patients when there are available caregivers but they are not assigned to that particular patient.

In an embodiment, the workflow stratification server 110 can escalate a call for care of a particular patient when all floor people are busy. The workflow stratification server 110 determines whether the call can be escalated to a supervisor level. By knowing where caregivers are using real-time tracking systems, the workflow stratification server 110 can escalate a call right away so a supervisor level can handle the call without having to wait for the customary 30 seconds before escalation. Conventionally, a wait time for a call to be answered is employed, and when the wait time is exceeded or timed out, then the call is escalated. The workflow stratification server 110 can monitor events within the hospital to determine whether it should wait for the timeout or escalate before the timeout. The server 110 can determine that there is no need to wait 30 seconds and instead just summon a supervisor to handle the call because it knows the assigned caregiver unavailable.

In an embodiment, the workflow stratification server 110 determines that two outstanding calls require a same caregiver to be at two rooms at the same time, i.e., the caregiver is called to both rooms simultaneously. The workflow stratification server 110 can then revise one of the outstanding calls to be handled by another caregiver unassigned to the rooms. That way, both calls can be tended to at the same time, and one patient does not have to wait while the other is being taken care of.

In a third exemplary system operation, the workflow stratification server 110 can help the patient in a hospital be more comfortable. The patient can indicate that his room is too hot, and when an event message is created by the nurse call devices 106 or the interface devices 108, the workflow stratification server 110 can remotely adjust the room thermostat. In this scenario, there is no need to send in a caregiver to adjust the thermostat. As such, caregiver resources are used more efficiently. A similar scenario is possible if the patient indicates that something is not working in the room, e.g., the television is not responding. The workflow stratification server 110 can attempt to cycle the television on and off, and perform simple troubleshooting. If simple troubleshooting does not work, then a maintenance order can be automatically populated or pre-populated without the need of caregiver assistance.

In a fourth exemplary system operation, the workflow stratification server 110 can determine, based on a cleaning schedule or based on a patient's request, that the patient's room needs to be cleaned. The workflow stratification server 110 can use event triggers like time of day, availability of cleaning personnel, staff utilization, and so on, to determine whether to send in a cleaning robot.

In each of the foregoing exemplary system operations, the workflow stratification server 110 adjusted a normal workflow based on detected changes within the hospital environment. Examples of changes that can be detected include changes to the patient, changes to a state or status of caregivers, changes to equipment associated with the patient, etc. The workflow stratification server 110 detects one or more changes and develops a suggested change to a normal or standard workflow, i.e., the server 110 suggests a rule change based on the changing environmental variables. The suggested rule change is presented to a system user, such as a caregiver, for implementation.

In an embodiment, the user devices 222 and workstations 226 provide human oversight when rule changes are suggested by the workflow stratification server 110. That is, once the server 110 identifies a new rule for the first time, instead of implementing the new rule the server 110 pings the user devices 222 and/or the workstations 226 for approval. That way, a new rule is not officially allowed until reviewed.

Figure 3:
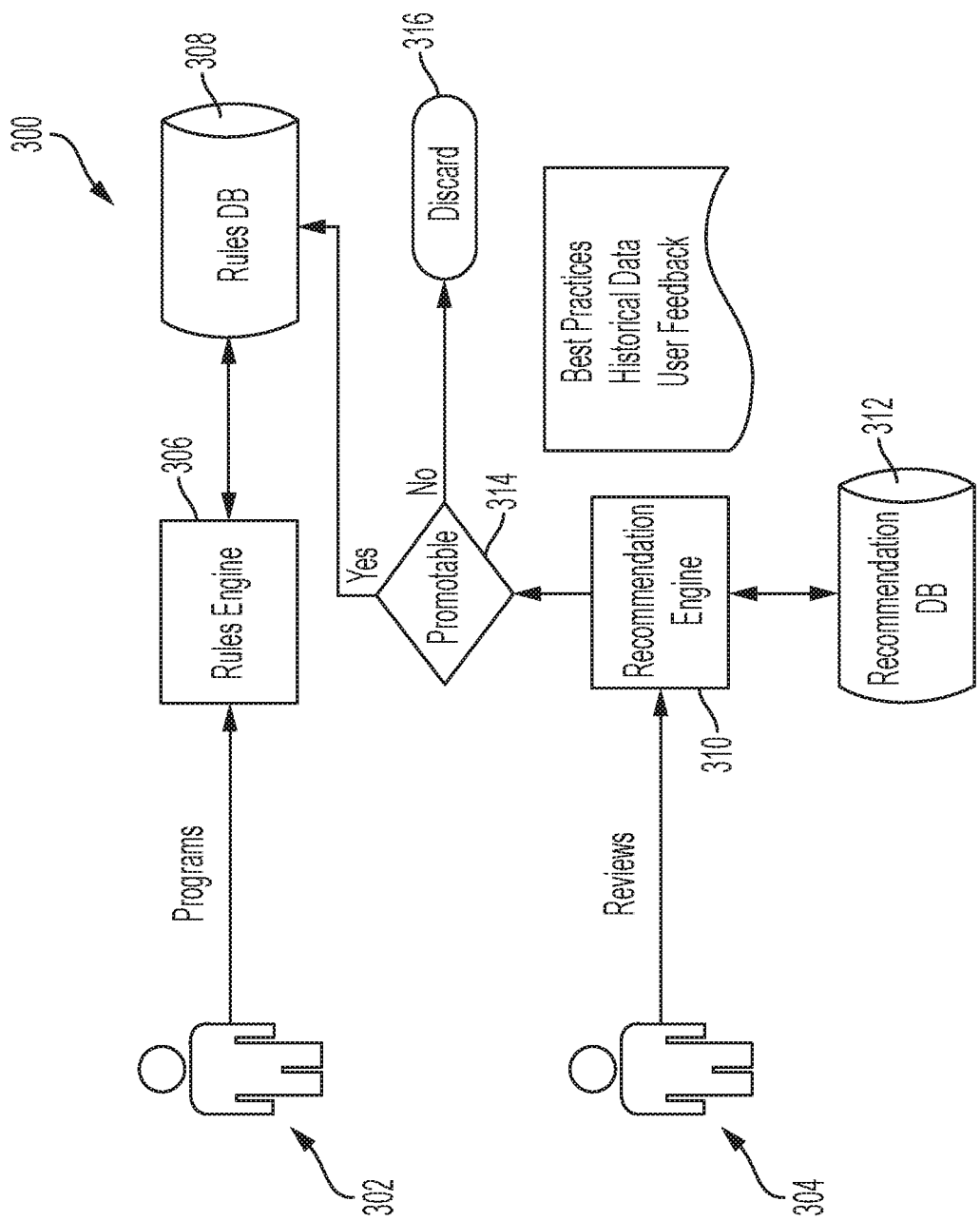
FIG. 3 illustrates a rule creation process for the workflow stratification server of FIG. 1, in accordance with a particular embodiment.

FIG. 3 illustrates a general process 300 undertaken within the rules engine 224 of the workflow stratification server 110 during creation of a rule, in accordance with a particular embodiment. FIG. 3 illustrates a rules engine 306 and a recommendation engine 310. In certain embodiments, these are sub-components of the rules engine 224 illustrated in FIG. 2. For clarity in explanation, these components are broken out for further discussion in relation to FIG. 3.

FIG. 3 includes two rule creation paths 302 and 304. Path 302 represents a rule created by a user programming the rule into the rules engine 306 for storage within the rules database 308 for future system use. In a particular embodiment, the rule will have the following data structure: Rule [ID, Name, Mutable, Triggers{ }, Actions { }]. The ID field is a unique identifier of the rule. The Name field is a user understandable text string describing the rule. The Mutable field indicates to the rules engine 306 that the workflow stratification server 110 is allowed to modify the rule to create a new rule based on learned behavior. The Triggers field indicates various clinical, technical, business and administrative triggers for the rule. The Actions field describes actions performed by the rule, such as activate an alarm, alert, notify or suppress some event, or update an audit log or forensic log. To manually create a rule, the user must define the various fields of the rule data structure and then store that rule in the rules database 308.

Alternatively, path 304 represents the process undertaken when the server 110 recommends a new rule based on system events and triggers and learned behavior. In particular embodiments, the workflow stratification server 110 can only recommend a new rule based on a pre-existing rule when the data structure of the pre-existing rule indicates that it can be modified in the Mutable field. In path 304, the recommendation engine 310 creates a new rule typically by modifying an existing rule based on various system events and triggers. The new rule is temporarily stored in a recommendation database 312 and then sent for user review. At step 314, the user receives indication of the new rule and can decide whether to promote the new rule or discard it at step 316. If the user promotes the new rule, then it is stored in the rules database 308 along with the user generated rules.

In an embodiment, a newly discovered rule need not be approved but can be applied broadly. That is, the new rule can be presented to a caregiver on user devices 222, workstations 226, and/or staff terminals. If the caregiver ignores the rule and deviates from the rule, then the workflow stratification server 110 determines that the rule is a bad rule and discards it. If the caregiver performs as provided in the new rule, then the workflow stratification server 110 determines that the rule is a good one. That way, performance or adoption of a rule can serve as feedback to validity of the rule.

Figure 4:
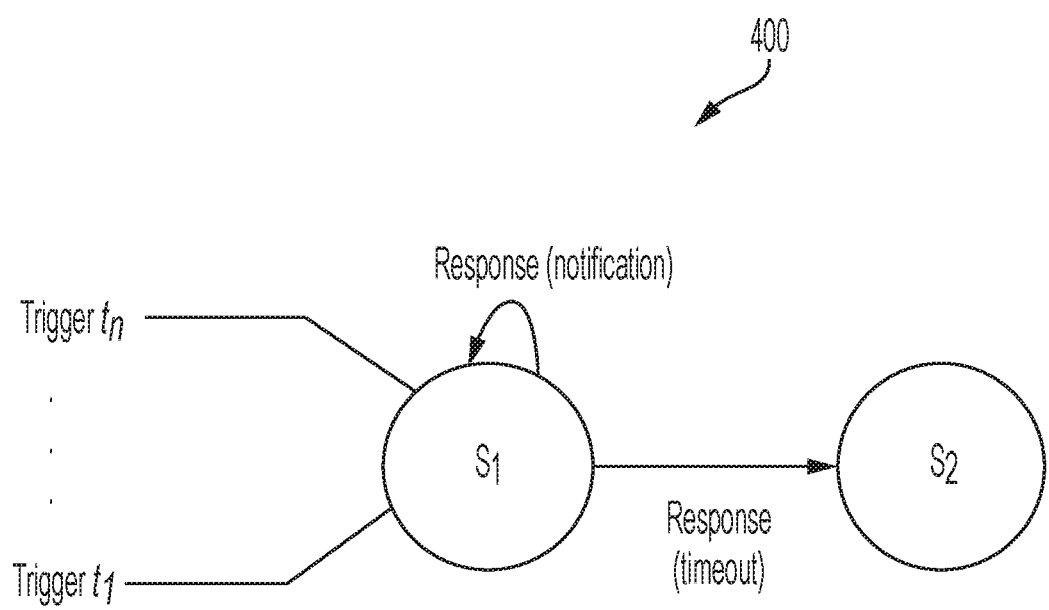
FIG. 4 illustrates a state diagram describing state transitions for a workflow stratification system according to embodiments of the disclosure.

FIG. 4 illustrates a state diagram 400 describing state transitions for a workflow stratification system according to embodiments of the disclosure. In FIG. 4, the workflow stratification server 110 can receive one or more triggers (Trigger $t_1$ to Trigger $t_n$). Each of these triggers can be event messages generated by the interface devices 108 and/or the nurse call devices 106. The workflow stratification server 110 can respond to triggers that do not merely indicate environmental status by notifying caregivers to take action. That is, triggers related to patient care and patient need, e.g., an active call, are to be responded to taking into account environmental status like available number of caregivers, closest caregiver, etc.

In the illustrated embodiment, the workflow stratification server 110 responding to active calls keeps the state in $S_1$, but when a call is not responded to in an allotted or predefined time, then a timeout pushes a transition to state $S_2$. In this instance, the workflow stratification server 110 can use learned behavior to decide what state $S_2$ should represent. For instance, in the above example of an active call, if a timeout occurs after some period of time with the call not being answered, then the call would typically be escalated for further review. However, in a particular embodiment, the workflow stratification server 110 may use information about the location of a caregiver from an RTLS system to inform it as to a proper state for $S_2$. For example, if the caregiver answers the call by walking into the room indicating the active call without manually updating the system, the workflow stratification server 110 may decide to update the active call to answered based on the caregivers location from the RTLS system even though the caregiver has not specifically updated the system manually.

The following chart represents a generic template for a state transition matrix.

|  |  | Current State | | |
| --- | --- | --- | --- | --- |
|  |  | S1 | S2 | S3 |
| Trigger Event | E1 | S2 | NA | NA |
|  | E2 | S2 | S3 | END |
|  | E3 | S1 | S3 | S3 |
|  | E4 | S2 | S3 | END |

As shown in the chart, this generic template includes four events: E1, E2, E3 and E4 and three states: S1, S2 and S3. Accordingly, this is a generic template for a system that can be in one of three states and transitions between these states based on an occurrence of one or more of events E1, E2, E3 and E4. In an exemplary embodiment, if the system is in state S1 and either events E1, E2 or E4 occur, then the system transitions to state S2; however, if event E3 happens, then the system stays in state S1. In the exemplary embodiment shown in the chart, once the system is in state S2, if any of events E2, E3 or E4 occur, then the system transitions to state S3; however, if event E1 occurs, then the state does not transition and a non-event or a mistake may be recorded by the system. In the exemplary embodiment shown in the chart, once the system is in state S3, if any of events E2 or E4 occur, then the system transitions to an END event that resets the system; however, if event E1 occurs, then the state does not transition and a non-event or a mistake may be recorded by the system. Additionally, if the event E3 occurs, then the system will stay in state S3.

In general, the above discussion of the generic template describes events state transitions based on event triggers that may be developed by the workflow stratification server 110 (see FIG. 1) according to embodiments of the disclosure. For instance, each of the state transitions may be suggested to a caregiver by the workflow stratification server 110 based on occurrence of one of the events E1-E4, where the caregiver will be asked to approve the state transition based on the event. If the caregiver approves of the state transition, then the workflow stratification server 110 may record the state transition and the event as a rule for subsequent use under similar conditions within the hospital system. In this manner, the workflow stratification server 110 can build rules for system operation.

Figure 5:
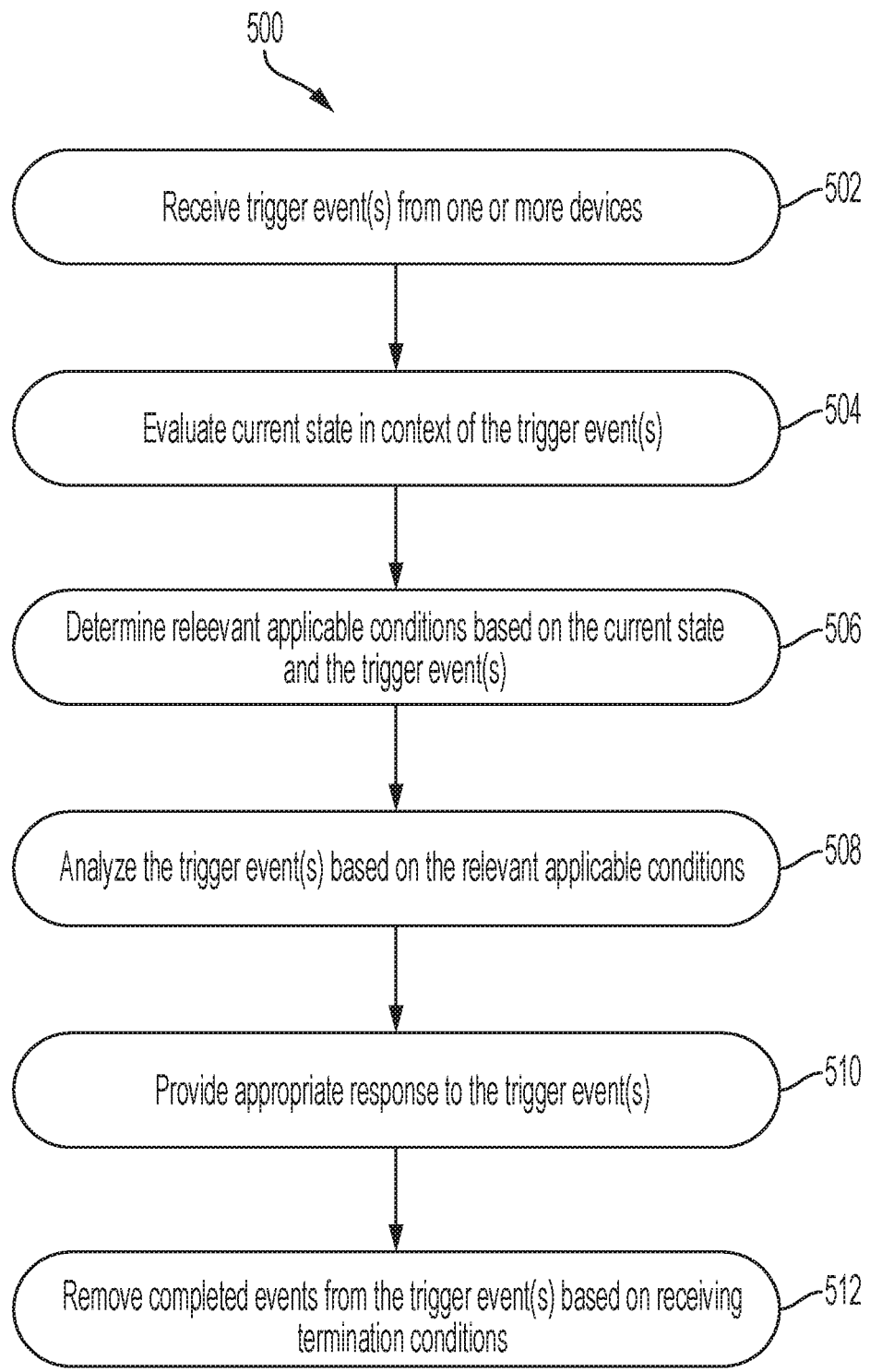
FIG. 5 illustrates a process performed by the workflow stratification server for managing patient care in a hospital environment accordingly to a particular embodiment.

FIG. 5 illustrates a process 500 performed by the workflow stratification server 110 for managing patient care in a hospital environment. In 502, the workflow stratification server 110 receives one or more trigger events from one or more devices, e.g., the interface devices 108 and the nurse call devices 106. These trigger events can take various forms, such as an alert for an event needing a staff response or a status request for events that are informational and do not require a in person response.

In some embodiments, the user devices 222 and the workstations 226 can provide additional information to be considered by the workflow stratification server, e.g., a caregiver logged into a workstation gives location of the specific caregiver, a caregiver's phone with GPS and wireless capability can provide location information to the workflow stratification server 110. Trigger events in 502 can include a call placed via a pullcord station, a staff terminal, a room console, a panic button, and so on.

Trigger events in 502 do not necessarily have to be emergency related. They can include a patient's preferences or a caregiver's preferences or category for the patient. The patient being categorized as a fall risk is one trigger that can be gleaned from the patient's medical record. The patient's eating schedule can also be a trigger event. Trigger event is used broadly to encompass information that can be obtained from devices in the hospital. In an embodiment, trigger events generated are categorized or flagged as clinical or non-clinical trigger events. In an embodiment, trigger events are categorized as clinical, business, and technical. For instance, in a particular embodiment, an event may be programmed in the system using the following data structure: Event=[Event ID, Event Name, Event Category, Event Priority, Event Parameters{ }]. The Event ID field is an identifier of the event within the system. The Event Name is a user understandable text string labeling the event. The Event Category field provides a category for the event, such as a clinical event, a technical event, a business event, or an administrative event. The Event Parameters field defines actions that must take place for that particular event within the hospital's internal network 100.

At 504, the workflow stratification server 110 evaluates future state in context of the trigger events obtained in 502. Triggers at 502 are obtained as individual events, but at 504, the server 110 begins grouping events together based on rules available to the rules engine 224. Historical data and previous responses can help in clustering trigger events that may be related to each other. A cluster of trigger events that merely provide environmental context comprise the current state. Outstanding calls for patient assistance are not included in the current state.

At 506, the workflow stratification server 110 determines relevant applicable conditions based on the current state and the trigger events of 502. Certain trigger events in the current state will be more dominating than others. For example, a fall risk patient getting out of bed is different from a non-fall risk patient getting out of bed. In the former, the current state of the patient being a fall risk heightens the importance of the activity of getting out of bed, while in the latter, the absence of a fall risk makes getting out of bed a non-factor event. At 506, the relevant applicable conditions are determined using data provided by a user. This data can be clinical, technical, business or administrative in nature. The workflow stratification server 110 utilizes this data in conjunction with a current state of relevant systems and equipment to determine the relevant application conditions.

At 508, the workflow stratification server 110 analyzes the trigger events based on the relevant applicable conditions. At 408, relevant applicable conditions are matched to trigger events to determine what steps should be taken. At 510, the workflow stratification server 110 provides appropriate responses to the trigger events. In an embodiment, the workflow stratification server 110 adjusts normal workflows for each trigger event based on its respective relevant applicable conditions. In an embodiment, the workflow stratification server proposes or recommends new rules or new workflows for a trigger event based on its applicable conditions.

In 512, the workflow stratification server 110 removes completed events from the trigger events based on receiving termination conditions. As calls are answered and certain triggers are no longer being reported to the workflow stratification server 110, the workflow stratification server 110 determines that the trigger event no longer applies and can update the current state.

Termination conditions can be determined on a priority level. For example, a caregiver can enter a room to respond to a call, and the caregiver must manually cancel the call, on a user device or a room console or some other device, once he is done responding to the call. In this example, the workflow stratification server 110 waits until the manual cancel signal is received from the caregiver before making the call as completed and removing the call from its tracked list of trigger events.

In another example, the caregiver responding to a call merely enters the patient's room, and after the workflow stratification server 110 receives via real time location services that the caregiver is in the patient's room, the server 110 marks the call as completed and removes the call from its tracked list of trigger events. This approach can be taken with low priority calls.

Figure 6:
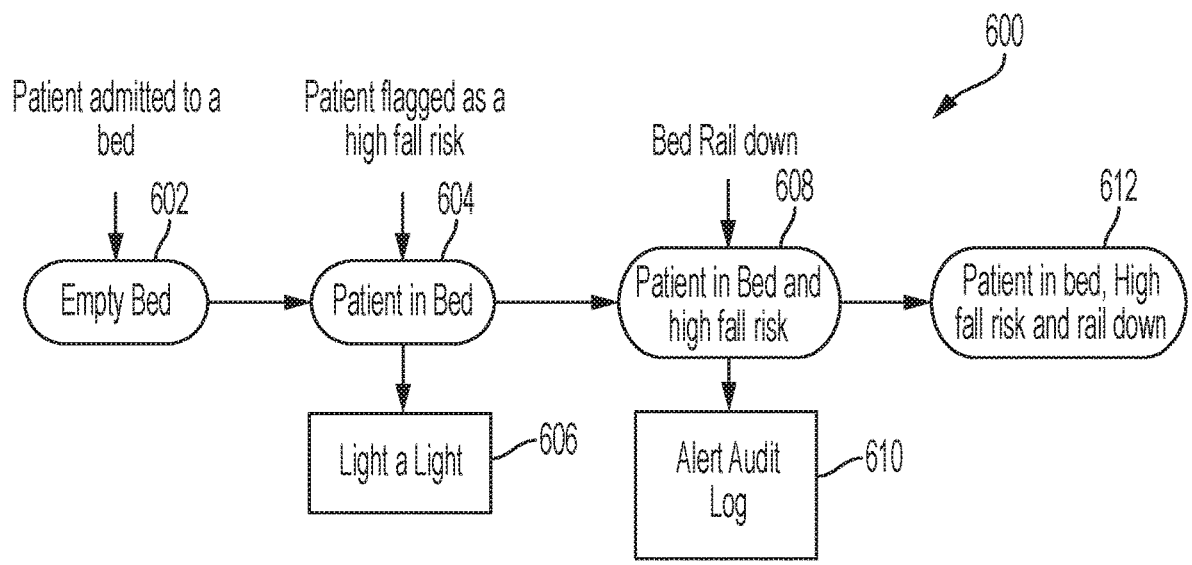
FIG. 6 illustrates a state diagram of an event processed by the workflow stratification server and nurse call system of FIG. 1, in accordance with an exemplary embodiment.
Figure 7:
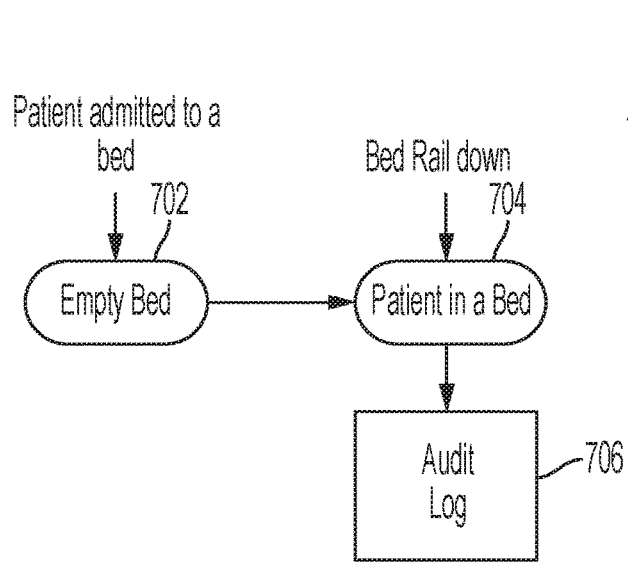
FIG. 7 illustrates a state diagram of an event processed by the workflow stratification server and nurse call system of FIG. 1, in accordance with an exemplary embodiment.

FIGS. 6 and 7 illustrate exemplary embodiments of state diagrams of event processing under different relevant applicable conditions, in accordance with certain embodiments of the disclosure. FIG. 6 illustrates a state diagram of an event process 600 for admitting a "fall risk" patient. At step 602, the "fall risk" patient is admitted to an empty bed. At step 604 the workflow stratification server 110 receives a "fall risk" status from an EMR system. At step 608, the workflow stratification server 110 maps the "fall risk" event to a nurse call equivalent and forwards it to the nurse call server, while recording this event in the audit database 232 at step 610. At step 612, the nurse call server 102 evaluates the notification targets, and if programmed, the nurse call server 102 will annunciate the fall risk on one or more nurse call devices 106, such as lighting on one or more segments of a corridor light.

In contrast to FIG. 6, FIG. 7 illustrates a state diagram of an event process 700 for admitting a patient that is not a "fall risk." At step 702, the patient is admitted to an empty bed. Because the patient is not a "fall risk," the workflow stratification server 110 is not updated with "fall risk" information from the EMR. Accordingly, at step 704, when the workflow stratification server 110 receives notification that a bed rail is down for this patient, the only action taken by the workflow stratification server 110 is to record the rail down event in the audit log 232 at step 706. In this embodiment, the workflow stratification server 110 does not need to modify any rule based on relevant applicable conditions because the rail being in an "up" or "down" configuration does not affect this particular patient.

Although trigger events and event messages are described in general, the workflow stratification system 110 can classify or categorize trigger events as one of three types: (1) clinical, (2) technical, and (3) business. Clinical events are events that relate to patient care, technical events relate to hospital equipment functionality and operation, and business events relate to business operations such as staffing conditions at certain shifts, etc.

Under the clinical framework, the workflow stratification server 110 can use caregiver location based on RTLS, phone location, pager location, etc. The staff location is used as an input for determining whether to change from a normal workflow. This could also be used when a caregiver goes "on break." Status type changes such that the workflow stratification server 110 flags another caregiver while the primary care giver is not available, and maintains this modified workflow until the primary comes back online. These types of modification to patient care related to clinical rules. Additional clinical inputs are available from hospital EMR system or any other hospital systems which give patient information.

An example of a technical rule is a rule that acts on a piece of nurse call equipment failing and some signaling event that could trigger a need for a technical review and changes to other workflows based on that equipment failure.

An example of a business rule is a rule that acts on a business trigger, e.g., knowing staffing aggregates. For example, if known beforehand that four people caregivers are to start their shift in the evening but only three staff members have logged into the system, then a trigger can be generated for rebalancing the workload of the staff members available. A rule recommendation can be provided that indicates that additional staff is needed and more patients should not be accepted or admitted. Business inputs can come from human resources systems such as hospital staff database.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A hospital network system deployed in a hospital environment, the hospital network system comprising:
   a plurality of interface devices associated with the hospital environment;
   a communication network coupled to each of the plurality of interface devices;
   a nurse call system comprising:
      a plurality of nurse call devices;
      a nurse call server configured to communicate with each of the plurality of nurse call devices; and
   a workflow stratification server for managing nurse call workflow within the hospital environment, the workflow stratification server is communicatively interposed between the nurse call system and the communication network such that the workflow stratification server evaluates and communicates workflow signaling between the plurality of interface devices and the nurse call system,
   wherein the workflow stratification server is configured to:
      receive event messages from the plurality of interface devices and from the plurality of nurse call devices;
      evaluate a current state of the nurse call system in context of the event messages, the current state of the nurse call system being a state of the nurse call system after evaluating an impact of the event messages;
      determine relevant applicable conditions for trigger events, the trigger events being a subset of the event messages;
      analyze the trigger events to determine a priority for responding to the trigger events, wherein the priority for responding to the trigger events is determined based on a state machine operating at the workflow stratification server, wherein the state machine evaluates a nurse call state based on the relevant applicable conditions and sets the priority for responding to the trigger events in view of a current state of the state machine; and
      remove one or more of the trigger events based on receiving termination conditions, and
      wherein the workflow stratification server manages the nurse call workflow for the hospital environment based on the nurse call state and the event messages.

2. The system of claim 1, wherein the event messages are classified as either clinical or non-clinical.

3. The system of claim 2, wherein the non-clinical classification includes technical and business.

4. The system of claim 1, wherein the plurality of nurse call devices includes a personal computer (PC) console, wherein the nurse call server is configured to receive termination conditions comprising a cancel alert event message from the PC console and relay the cancel alert event message to the workflow stratification server.

5. The system of claim 1, wherein the plurality of integrated devices includes a mobile phone, wherein the workflow stratification server is configured to receive terminal conditions comprising location data from the mobile phone, the location data indicating the mobile phone is at a specific area in the hospital environment.

6. The system of claim 1, wherein the event messages comprise a patient's clinical condition, malfunction of medical devices, malfunction of entertainment devices, and number of caregivers in a specified location.

7. The system of claim 6, wherein the trigger events comprise a call from a patient's room, and the workflow stratification server escalates the call based on the patient's clinical condition.

8. The system of claim 1, wherein the plurality of interface devices comprises one or more of a bed management gateway, an electronic medical records (EMR) interface engine, an physiological monitor, and a mobile signaling application gateway.

9. The system of claim 1, wherein the plurality of nurse call devices comprises one or more of a Session Initiation Protocol (SIP) interface, a personal computer (PC) console, a TAP interface, a patient station, and a staff terminal.

10. The system of claim 1, wherein a machine learning algorithm is used to analyze how trigger events relate to their respective applicable conditions and revise the state of the nurse call system.

11. A method for automatically managing nurse call workflow within a hospital environment including a plurality of interface devices, a communication network coupled to each of the plurality of interface devices, a nurse call system including a nurse call server and a plurality of nurse call devices communicatively coupled to the nurse call sever, and a workflow stratification server for managing workflows within the hospital environment, the workflow stratification server being communicatively interposed between the nurse call system and the communication network such that the workflow stratification server evaluates and communicates workflow signaling between the plurality of interface devices and the nurse call system, the method, performed by the workflow stratification server, comprises:
   receiving event messages from the plurality of interface devices and from the plurality of nurse call devices;
   evaluating a current state of the nurse call system in context of the event messages, the current state of the nurse call system being a state of the nurse call system after evaluating an impact of the event messages;
   determining relevant applicable conditions for trigger events, the trigger events being a subset of the event messages;
   analyzing the trigger events to determine a priority for responding to the trigger events, wherein the priority for responding to the trigger events is determined based on a state machine operating at the workflow stratification server, wherein the state machine evaluates a nurse call state based on the relevant applicable conditions and sets the priority for responding to the trigger events in view of a current state of the state machine; and
   removing one or more of the trigger events based on receiving termination conditions,
   wherein the workflow stratification server manages the nurse call workflow for the hospital environment based on the nurse call state and the event messages.

12. The system of claim 11, wherein the event messages are classified as either clinical or non-clinical.

13. The system of claim 12, wherein the non-clinical classification includes technical and business.

14. The system of claim 11, wherein the plurality of nurse call devices includes a personal computer (PC) console, wherein the nurse call server is configured to receive termination conditions comprising a cancel alert event message from the PC console and relay the cancel alert event message to the workflow stratification server.

15. The system of claim 11, wherein the plurality of integrated devices includes a mobile phone, wherein the workflow stratification server is configured to receive terminal conditions comprising location data from the mobile phone, the location data indicating the mobile phone is at a specific area in the hospital environment.

16. The system of claim 11, wherein the event messages comprise a patient's clinical condition, malfunction of medical devices, malfunction of entertainment devices, and number of caregivers in a specified location.

17. The system of claim 16, wherein the trigger events comprise a call from a patient's room, and the workflow stratification server escalates the call based on the patient's clinical condition.

18. The system of claim 11, wherein the plurality of interface devices comprises one or more of a bed management gateway, an electronic medical records (EMR) interface engine, an physiological monitor, and a mobile signaling application gateway.

19. The system of claim 11, wherein the plurality of nurse call devices comprises one or more of a Session Initiation Protocol (SIP) interface, a personal computer (PC) console, a TAP interface, a patient station, and a staff terminal.

20. A workflow stratification server for managing nurse call workflow within a hospital environment, the hospital environment including a plurality of interface devices, a communication network coupled to each of the plurality of interface devices, a nurse call system including a nurse call server and a plurality of nurse call devices communicatively coupled to the nurse call sever, wherein the workflow stratification server is communicatively interposed between the nurse call system and the communication network such that the workflow stratification server evaluates and communicates workflow signaling between the plurality of interface devices and the nurse call system , the workflow stratification server comprising:

a processor; and
 a memory storing instructions that when executed by the processor configure the workflow stratification server to perform steps comprising:
  receiving event messages from the plurality of interface devices and from the plurality of nurse call devices;
  evaluating a current state of the nurse call system in context of the event messages, the current state of the nurse call system being a state of the nurse call system after evaluating an impact of the event messages;
  determining relevant applicable conditions for trigger events, the trigger events being a subset of the event messages ;
  analyzing the trigger events to determine a priority for responding to the trigger events, wherein the priority for responding to the trigger events is determined based on a state machine operating at the workflow stratification server, wherein the state machine evaluates a nurse call state based on the relevant applicable conditions and sets the priority for responding to the trigger events in view of a current state of the state machine; and
  removing one or more of the trigger events based on receiving termination conditions;
 wherein the workflow stratification server manages the nurse call workflow for the hospital environment based on the nurse call state and the event messages.

\* \* \* \* \*